United States Patent
Morrone et al.

(10) Patent No.: US 12,412,638 B2
(45) Date of Patent: Sep. 9, 2025

(54) STRUCTURE-BASED, LIGAND ACTIVITY PREDICTION USING BINDING MODE PREDICTION INFORMATION

(71) Applicant: International Business Machines Corportion, Armonk, NY (US)

(72) Inventors: Joseph Anthony Morrone, Pleasantville, NY (US); Jeffrey Kurt Weber, Brooklyn, NY (US); Sugato Bagchi, White Plains, NY (US); Wendy Dawn Cornell, Warren, NJ (US)

(73) Assignee: International Business Machines Corporation, Armonk, NY (US)

( * ) Notice: Subject to any disclaimer, the term of this patent is extended or adjusted under 35 U.S.C. 154(b) by 1193 days.

(21) Appl. No.: 17/166,483

(22) Filed: Feb. 3, 2021

(65) Prior Publication Data

US 2022/0246233 A1 Aug. 4, 2022

(51) Int. Cl.
  *G16B 15/30* (2019.01)
  *G06N 3/045* (2023.01)
  *G06N 3/08* (2023.01)

(52) U.S. Cl.
  CPC ............ *G16B 15/30* (2019.02); *G06N 3/045* (2023.01); *G06N 3/08* (2013.01)

(58) Field of Classification Search
  CPC ........... G16B 15/30; G06N 3/045; G06N 3/08
  See application file for complete search history.

(56) References Cited

U.S. PATENT DOCUMENTS 6,587,845 B1 * 7/2003 Braunheim ............ G16C 20/70
  706/20
9,373,059 B1    6/2016 Heifets et al.
(Continued)

FOREIGN PATENT DOCUMENTS

CN   112837747 A * 5/2021 ............. G16B 20/30

OTHER PUBLICATIONS

Stepniewska-Dziubinska, Marta M., Piotr Zielenkiewicz, and Pawel Siedlecki. "Development and evaluation of a deep learning model for protein-ligand binding affinity prediction." Bioinformatics 34, No. 21 (2018): 3666-3674. (Year: 2018).*

(Continued)

*Primary Examiner* — Casey R. Garner
(74) *Attorney, Agent, or Firm* — Scully, Scott, Murphy & Presser, P.C.

(57) ABSTRACT

A system and method for structure-based, small molecule activity prediction using binding mode prediction information. Binding scores between ligands and target molecules, (e.g. proteins, RNA, DNA, lipids, sugars) are first generated using molecular docking. A first machine learned deep neural network (DNN) model is developed using data representing the molecular ligand-target pair 3D structures and docking features to predict binding modes. Using transfer learning, weights of layers learned in the first machine learned model are used as weights in layers of a second machine learned DNN model used to more accurately improve the performance of activity prediction of the second machine learned model. For a target newly paired ligand-target complex, the method further implements a binding mode selector for selecting one or more particular binding poses for input to the activity prediction model for use in activity mode prediction of an activity of the target paired ligand-protein complex.

20 Claims, 10 Drawing Sheets

(56) References Cited

U.S. PATENT DOCUMENTS

| | | | |
|---|---|---|---|
| 2003/0131015 A1 | 7/2003 | Chen | |
| 2005/0053999 A1* | 3/2005 | Gough | C40B 30/04 |
| | | | 435/6.16 |
| 2014/0303952 A1 | 10/2014 | Wang et al. | |
| 2018/0285731 A1 | 10/2018 | Heifets et al. | |
| 2019/0050537 A1* | 2/2019 | Luo | G16H 70/40 |
| 2020/0342953 A1 | 10/2020 | Morrone et al. | |
| 2022/0036966 A1* | 2/2022 | Meyers | G16B 15/30 |
| 2023/0360734 A1* | 11/2023 | Evans | G16B 15/20 |
| 2023/0402133 A1* | 12/2023 | Jumper | G16B 15/30 |

OTHER PUBLICATIONS

Rueda et al., "Best Practices in Docking and Activity Prediction." bioRxiv (2016): 039446, bioRxiv preprint first posted online Feb. 12, 2016; doi: http://dx.doi.org/10.1101/039446, 16 pages.

Di Lena et al., "Deep architectures for protein contact map prediction." Bioinformatics 28.19 (2012), revised on Jul. 5, 2012; accepted on Jul. 22, 2012, pp. 2449-2457.

Gohlke et al., "Approaches to the description and prediction of the binding affinity of small-molecule ligands to macromolecular receptors." Angewandte Chemie International Edition 41.15 (2002): First Published Aug. 2, 2002, pp. 2644-2676.

Jimenez et al. "KDEEP: Protein-Ligand Absolute Binding Affinity Prediction via 3D-Convolutional Neural Networks." Journal of chemical information and modeling 58.2 (2018): Downloaded via IBM Corp on Jan. 24, 2020 at 00:45:09 (UTC); See https://pubs.acs.org/sharingguidelines for options on how to legitimately share published articles pp. 287-296.

Lusci et al., "Deep architectures and deep learning in chemoinformatics: the prediction of aqueous solubility for drug-like molecules." Journal of chemical information and modeling 53.7 (2013): Downloaded via IBM Corp on Jan. 24, 2020 at 00:55:10 (UTC).See https://pubs.acs.org/sharingguidelines for options on how to legitimately share published articles., pp. 1563-1575.

Morrone, et al. "Combining docking pose rank and structure with deep learning improves protein-ligand binding mode prediction." arXiv preprint arXiv:1910.02845 (2019), Oct. 2019, 13 pages.

Lim et al., "Predicting Drug-Target Interaction Using a Novel Graph Neural Network with 3D Structure-Embedded Graph Representation", J. Chem. Inf. Model. 2019, 59, Published: Aug. 23, 2019, pp. 3981-3988.

Ragoza et al., "Protein-Ligand Scoring with Convolutional Neural Networks", J. Chem. Inf. Model. 2017, 57, Published: Apr. 3, 2017,pp. 942-957.

Trott et al., "AutoDock Vina: improving the speed and accuracy of docking with a new scoring function, efficient optimization and multithreading", J Comput Chem. Jan. 30, 2010; 31(2): pp. 455-461.

Wallach et al., "AtomNet: A Deep Convolutional Neural Network for Bioactivity Prediction in Structure-based Drug Discovery", arXiv:1510.02855v1 [cs.LG] Oct. 10, 2015, 11 pages.

Francoeur et al., "Three-Dimensional Convolutional Neural Networks and a Cross-Docked Data Set for Structure-Based Drug Design", https://dx.dio.org/10.1021/acs.jcim.0c00411; Published: Aug. 31, 2020, 16 pages.

Feinberg, et al., PotentialNet for Molecular Property Prediction, ACS Central Science, Nov. 2, 2018, vol. 4, Issue 11, pp. 1520-1530.

Friesner, et al., Glide: A New Approach for Rapid, Accurate Docking and Scoring. 1. Method and Assessment of Docking Accuracy, Journal of Medicinal Chemistry Feb. 27, 2004, vol. 47, Issue 7, pp. 1739-1749.

Jones, et al., Development and Validation Of A Genetic Algorithm For Flexible Docking, J Mol Biol, Apr. 4, 1997, vol. 267, Issue 3, pp. 727-748.

Kuntz, et al., A Geometric Approach To Macromolecule-Ligand Interactions, Journal Of Molecular Biology, Oct. 25, 1982, vol. 161, Issue 2, pp. 269-288.

Nguyen, et al., Mathematical Deep Learning for Pose and Binding Affinity Pre- diction and Ranking in D3R Grand Challenges, J Comput Aided Mol Des, Jan. 2019, vol. 33, Issue 1, pp. 77-82.

Pereira, et al., Boosting Docking-Based Virtual Screening with Deep Learning, Journal of Chemical Information and Modeling, Nov. 4, 2016, vol. 56, Issue 12, 18 pages.

* cited by examiner

500

414

505

| | PROTEIN 1 | PROTEIN 2 | PROTEIN 3 | ... |
|---|---|---|---|---|
| Ligand 1 | Bind. mode graph 1,1 | Bind. mode graph 1,2 | Bind. mode graph 1,3 | |
| Ligand 2 | Bind. mode graph 2,1 | Bind. mode graph 2,2 | Bind. mode graph 2,3 | |
| Ligand 3 | ⋮ | ⋮ | ⋮ | |
| Ligand 4 | ⋮ | ⋮ | ⋮ | |
| Ligand 5 | Bind. mode graph 5,1 | Bind. mode graph 5,2 | Bind. mode graph 5,3 | |
| ... | | | | |

| | Bind. mode graph 1,1 | Bind. mode graph 1,2 | Bind. mode graph 1,3 | ... |
|---|---|---|---|---|
| Ligand-protein pair 1 | Distance 1,1 | Distance 1,2 | Distance 1,3 | |
| Ligand-protein pair 2 | Distance 2,1 | Distance 2,2 | Distance 2,3 | |
| Ligand-protein pair 3 | ⋮ | ⋮ | ⋮ | |
| Ligand-protein pair 4 | ⋮ | ⋮ | ⋮ | |
| Ligand-protein 5 | Distance 5,1 | Distance 5,2 | Distance 5,3 | |
| ... | | | | |

STRUCTURE-BASED, LIGAND ACTIVITY PREDICTION USING BINDING MODE PREDICTION INFORMATION

FIELD

The present invention relates generally to machine-learning systems and methods for predicting activity of molecules, and in particular, to systems and methods for structure-based, ligand activity prediction using binding mode prediction.

BACKGROUND

In the biotech field, docking programs are a standard tool for structure-based activity prediction that typically use physics-inspired or machine learned scoring functions to sample three-dimensional coordinates (binding modes) or predict activity given a protein structure and a ligand.

In order to improve predictions, methods that combine deep learning neural networks with structural data or the output of docking have been explored. These models can be trained to yield predictions.

However, such methods have been plagued by issues of dataset bias (and corresponding irrelevance of protein-related features) for the task of activity prediction. Therefore, their utility is still an open question.

One significant pitfall of these methods is that 'incorrect' poses are randomly distributed throughout datasets of generated docked structures. Therefore, the contacts that active ligands make with proteins are misrepresented. Activity datasets often do not contain structural information on how the ligand binds to its target.

SUMMARY

A system, method and computer program product for more accurately predicting activity of ligands, including small molecules and biologics against target molecules, including proteins, RNA, DNA, sugars and lipids.

A system, method and computer program product for improving the performance of an activity prediction model by incorporating a reliable binding mode prediction model that learns how ligands bind to target molecules and applying this knowledge to activity prediction.

The system, method and computer program product for improving the performance of an activity prediction model that implements transfer learning techniques and/or the design of a binding mode selector.

In an embodiment, the system, method and computer program product implements transfer learning techniques and/or the design of a binding mode selector operating in conjunction with the output of a docking program. Transfer learning applies knowledge gained from structural datasets to the task of activity prediction where structural training data is often not available.

In one aspect, there is provided a computer-implemented method of predicting an activity of a ligand against a target molecule. The method comprises: receiving a representation of a ligand molecule and a target molecule forming a ligand-target molecule pair structure for which an activity is to be determined; obtaining one or more binding modes corresponding to the received ligand-target molecule pair structure; determining, using a first neural network, a confidence metric characterizing a correctness of each of the obtained one or more binding modes; selecting one or more binding modes based on their corresponding characterizing metrics; inputting, to a second neural network, as input features, the selected one or more binding modes; and determining, using the second neural network, a prediction of an activity for the ligand-target molecule pair structure.

In a further aspect, there is provided a computer system for predicting an activity of a ligand against a target molecule. The system comprises: a memory storage device; and a hardware processor coupled to the memory storage device and configured to perform a method to: receive a representation of a ligand molecule and a target molecule forming a ligand-target molecule pair structure for which an activity is to be determined; obtain one or more binding modes corresponding to the received ligand-target molecule pair structure; determine, using a first neural network, a confidence metric characterizing a correctness of each of the obtained one or more binding modes; select one or more binding modes based on their corresponding characterizing metrics; input, to a second neural network, as input features, the selected one or more binding modes; and determine, using the second neural network, a prediction of an activity for the ligand-target molecule pair structure.

In a further aspect, there is provided a computer program product for performing operations. The computer program product includes a storage medium readable by a processing circuit and storing instructions run by the processing circuit for running a method. The method is the same as listed above.

BRIEF DESCRIPTION OF THE SEVERAL VIEWS OF THE DRAWINGS

FIG. 5A is an example visualization of a feature data matrix (a 2-D matrix) that includes the ligands (e.g., drugs) as rows, the target proteins as columns, and the featurized data as a graph representing 3D coordinates of the binding mode of a protein-ligand pair structure;

FIG. 5B illustrate an example visualization of a distance label training matrix for use in training the binding mode prediction model in an embodiment;

DETAILED DESCRIPTION

A system, method and computer program product for improving the performance of an activity prediction model. The system and method combines a binding mode prediction model with an activity prediction model that can improve the performance of the activity prediction model.

The binding mode prediction model systematically improves the performance of the activity prediction model for the prediction of ligand activity by using transfer learning between the binding mode prediction and activity prediction models and use of a binding mode selector that selects a binding mode, informed by the binding mode prediction model, from the ensemble of poses generated by docking. This can be used in conjunction with transfer learning concepts. As referred to herein, "ligands" are any type of molecule that binds to target which includes, but are not limited to, small organic molecules and biologics. A "Target" or "target molecule" includes, but is not limited to: proteins or molecular structures such as RNA, DNA, cellular membranes, sugars, lipids, etc.

Figure 1:
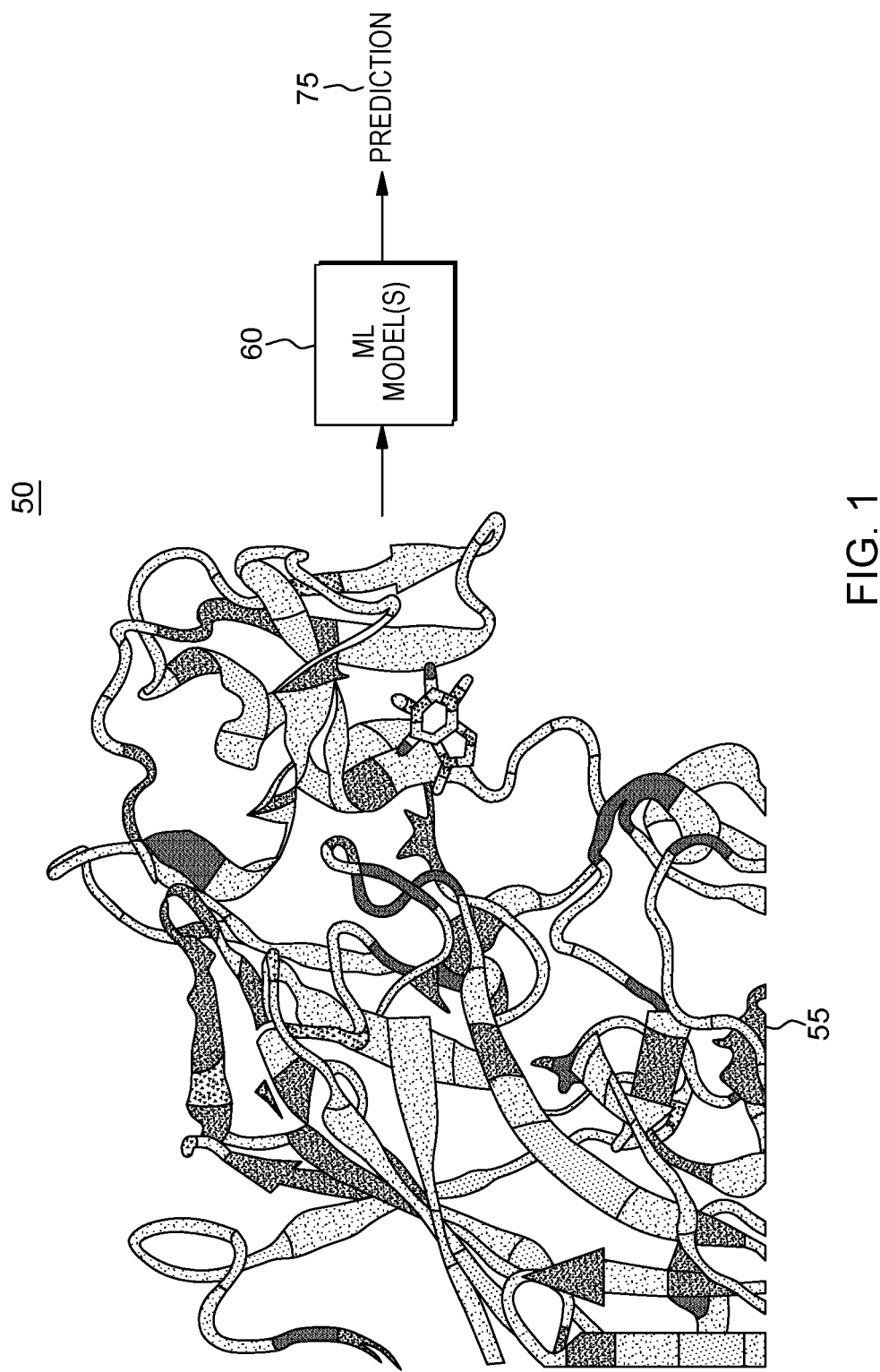
FIG. 1 depicts a simple schematic representing a three-dimensional binding mode of the protein-ligand complex serving as inputs to deep learning models to yield various predictions.

FIG. 1 depicts a simple schematic 50 of a three-dimensional binding mode of the protein-ligand complex 55 that serves as input to one or more deep learning models 60 to yield various predictions 75, for example of activity and of binding mode confidence. Both activity prediction and binding mode prediction models may be trained deep neural network (DNN) models.

In an embodiment, the improving the performance of the activity prediction model is achieved by: using transfer learning by incorporating weights pre-trained on binding mode prediction into the activity prediction model. Using a binding mode selector to choose reliable poses: such a selector can use the binding mode prediction model to choose poses, and/or employ direct comparisons with experiment and/or consensus models. In embodiments, some combination of transfer learning and binding mode selection can be used.

In an embodiment, for activity model training, various datasets can be fed into the model including: a) single protein target; b) targets within a protein family; and c) a number of targets sampled across protein families.

Figure 2:
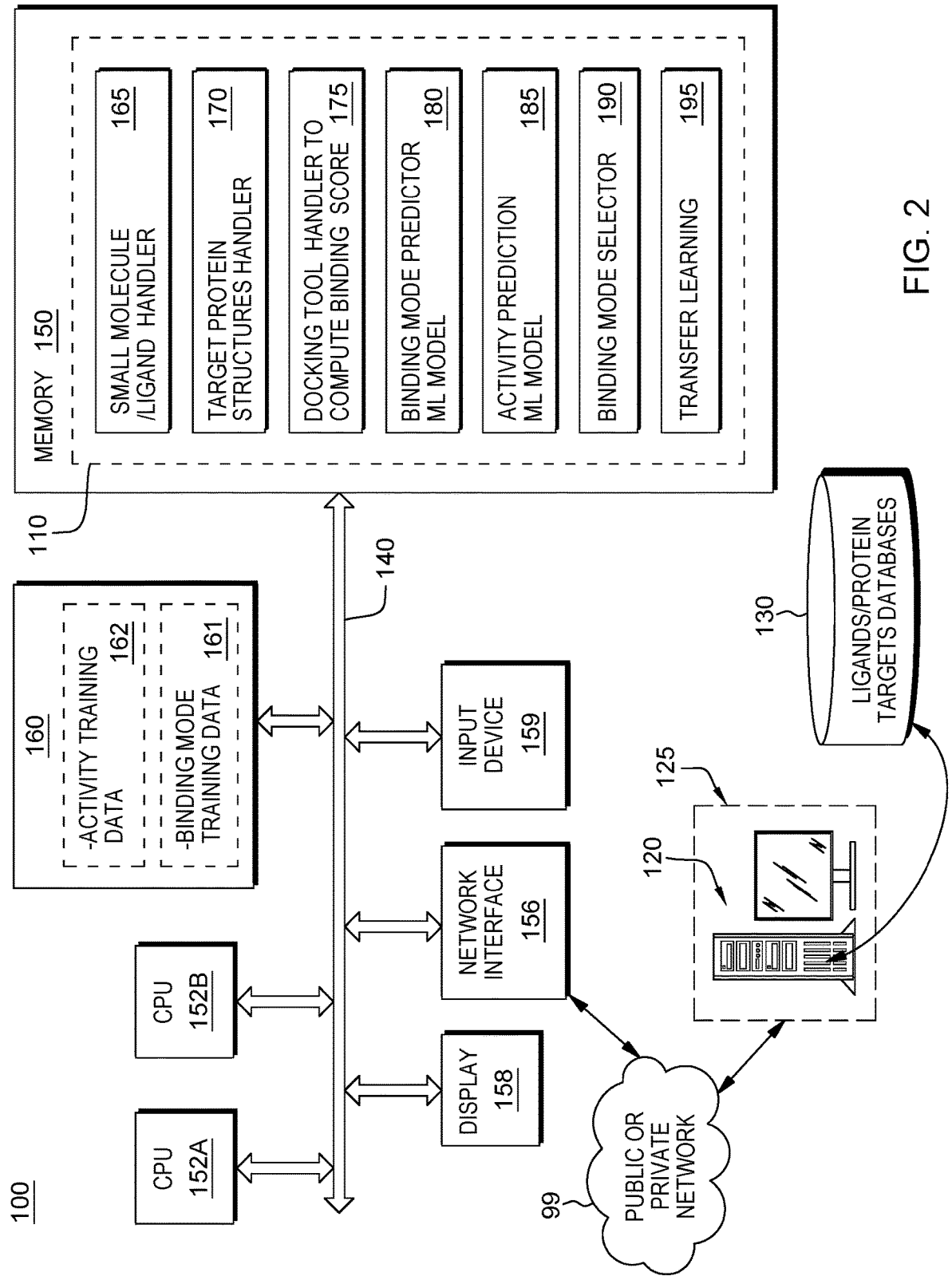
FIG. 2 schematically shows an exemplary computer system/computing device which is applicable to implement the embodiments for improving the performance of an activity prediction model according to one embodiment.

FIG. 2 depicts a computer system 100 for improving the performance of an activity prediction model according to one embodiment. In some aspects, system 100 may include a computing device, a mobile device, or a server. In some aspects, computing device 100 may include, for example, personal computers, laptops, tablets, smart devices, smart phones, or any other similar computing device.

Computing system 100 includes one or more hardware processors 152A, 152B, a memory 150, e.g., for storing an operating system and application program instructions, a network interface 156, a display device 158, an input device 159, and any other features common to a computing device. In some aspects, computing system 100 may, for example, be any computing device that is configured to communicate with one or more web-sites 125 including a web- or cloud-based server 120 over a public or private communications network 99. For instance, a web-site 125 may include the commercially available PubChem® (registered trademark of the National Library of Medicine) database resource (available at pubchem.ncbi.nlm.nih.gov) that provides ligands/small molecules (i.e. chemical, pharmacological and pharmaceutical) data and other chemical information. Alternately, or in addition, web-site 125 may include the commercially available PDBbind database resource (e.g., www.pdbbind-cn.org) which collects experimentally measured binding affinity data (e.g., Kd, Ki and IC50) and coordinates for protein-ligand complexes deposited in the Protein Data Bank (rcsb.org) that collects three-dimensional structural data of large biological molecules, such as proteins.

Further, as shown as part of system 100, there is provided a local memory useful for the binding mode and activity prediction processing which may include an attached memory storage device 160, or a remote memory storage device, e.g., a database, accessible via a remote network connection for input to the system 100.

In the embodiment depicted in FIG. 2, processors 152A, 152B may include, for example, a microcontroller, Field Programmable Gate Array (FPGA), or any other processor that is configured to perform various operations. Additionally shown are the communication channels 140, e.g., wired connections such as data bus lines, address bus lines, Input/Output (I/O) data lines, etc., for routing signals between the various components of system 100. Processors 152A, 152B are configured to execute method instructions as described below. These instructions may be stored, for example, as programmed modules in a further associated memory storage device 150.

Memory 150 may include, for example, non-transitory computer readable media in the form of volatile memory, such as random access memory (RAM) and/or cache memory or others. Memory 150 may include, for example, other removable/non-removable, volatile/non-volatile storage media. By way of non-limiting examples only, memory 150 may include a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Network interface 156 is configured to transmit and receive data or information to and from a web-site server 120, e.g., via wired or wireless connections. For example, network interface 156 may utilize wireless technologies and communication protocols such as Bluetooth®, WIFI (e.g., 802.11a/b/g/n), cellular networks (e.g., CDMA, GSM, M2M, and 3G/4G/4G LTE), near-field communications systems, satellite communications, via a local area network (LAN), via a wide area network (WAN), or any other form of communication that allows computing device 100 to transmit information to or receive information from the server 120.

Display 158 may include, for example, a computer monitor, television, smart television, a display screen integrated into a personal computing device such as, for example, laptops, smart phones, smart watches, virtual reality headsets, smart wearable devices, or any other mechanism for displaying information to a user. In some aspects, display 158 may include a liquid crystal display (LCD), an e-paper/e-ink display, an organic LED (OLED) display, or other similar display technologies. In some aspects, display 158 may be touch-sensitive and may also function as an input device.

Input device 159 may include, for example, a keyboard, a mouse, a touch-sensitive display, a keypad, a microphone, or other similar input devices or any other input devices that may be used alone or together to provide a user with the capability to interact with the computing device 100.

With respect to configuring the computer system 100 as a tool for more accurately predicting ligand activity to accelerate drug discovery, the local or remote memory 160 may be configured for temporarily storing ligand-target protein data including corresponding ligand-target protein binding pose prediction model training data 161 and activity training data 162 for training the respective binding mode and activity prediction models. Representations of small molecules or ligands can be formatted as various representations, for example: ASCII text-strings such as obtained via a SMILES (Simplified Molecular-Input Line-Entry System) web-based interface, molecular graphs, and cartesian coordinate files in the PDB file format. Alternately or in addition, the representations of small molecules can be stored in a local memory attached to the computer system 100.

As mentioned, memory 150 of computer system 100 further stores processing modules that include programmed instructions adapted to invoke operations for more accurately predicting activity of new ligand-protein complexes to accelerate drug discovery.

In one embodiment, one of the programmed processing modules stored at the associated memory 150 include a module 165 that is provided with computer readable instructions, data structures, program components and application interfaces for searching/collecting small molecule or ligand data from a PubChem® or like data source 130 and/or for receiving structures of ligands derived from other sources. In an embodiment, this module can further invoke methods to transform collected small molecule data for an existing or known drug structure into a one-dimensional ASCII string representation via a SMILEs API for use by the system.

A further programmed processing module includes a target protein handler module 170 provided with computer readable instructions, data structures, program components and application interfaces for interacting with the PDBbind database web-site for selecting and processing structures of target proteins and/or for receiving structures of proprietary target proteins derived from other sources.

A further programmed processing module includes a docking tool handler module 175 that is provided with computer readable instructions, data structures, program components and application interfaces for interacting with the AutoDock Vina docking program or like docking programs to generate the molecular binding scores between ligands and selected target proteins that are input to and used by other prediction model components.

In one embodiment, another programmed processing module stored at the associated memory 150 of system tool 100 employs instructions to configure the system to build and run a supervised binding mode prediction machine learning (ML) model 180. The binding mode prediction model 180 can include a deep learning neural network (DNN) model such as a convolution neural network (CNN), a graph CNN, a multi-layer perceptron (MLP) or a recurrent neural network (RNN). The deep learning models can be written in Python using the TensorFlow library. This binding mode prediction ML model is trained to provide a confidence measure that an input binding mode of a ligand-target protein complex is in a correct conformation. In an embodiment, the binding mode prediction model can include the DNN described in applicant's commonly-owned, co-pending U.S. patent application Ser. No. 16/397,003, the whole contents and disclosure of which is incorporated by reference as if fully set forth herein.

Another programmed processing module stored at the associated memory 150 employs instructions to configure the system to build and run a supervised activity prediction ML model 185 is trained to predict an activity of a particular ligand-target protein complex pair. This model can include a deep learning neural network model such as a CNN, MLP or RNN. The activity prediction ML model 185 is trained to output an activity prediction that: can be formulated as a classification, as a regression, and can be used for predicting a toxicity feature, for example.

A further programmed processing module includes a binding mode selector module 190 including computer readable instructions, data structures, program components and application interfaces implementing rules for selecting one or more binding mode poses from an input set of ligand-protein binding poses according to a user-defined criteria in order to choose a most correct binding mode for an activity relevant dataset, i.e., a most correct in the sense of highest correctness/confidence or plausibility. The output binding mode of the selector module 190 is used as an input(s) for training the activity prediction model.

A further programmed processing module stored at the associated memory 150 include a transfer learning module 195 providing computer readable instructions, data structures, program components and application interfaces for enabling transfer learning between the binding mode prediction and activity prediction models as one means of improving predictions of activity. As referred to herein, transfer learning module 195 implements the machine learning concept of applying the knowledge gained from solving one problem to a different (related) problem/task. In the context of deep learning, this is achieved by taking the weights obtained from neural network layers trained on one binding mode prediction task and then importing them into the activity prediction neural network model tailored towards a different task (activity prediction).

Figure 3:
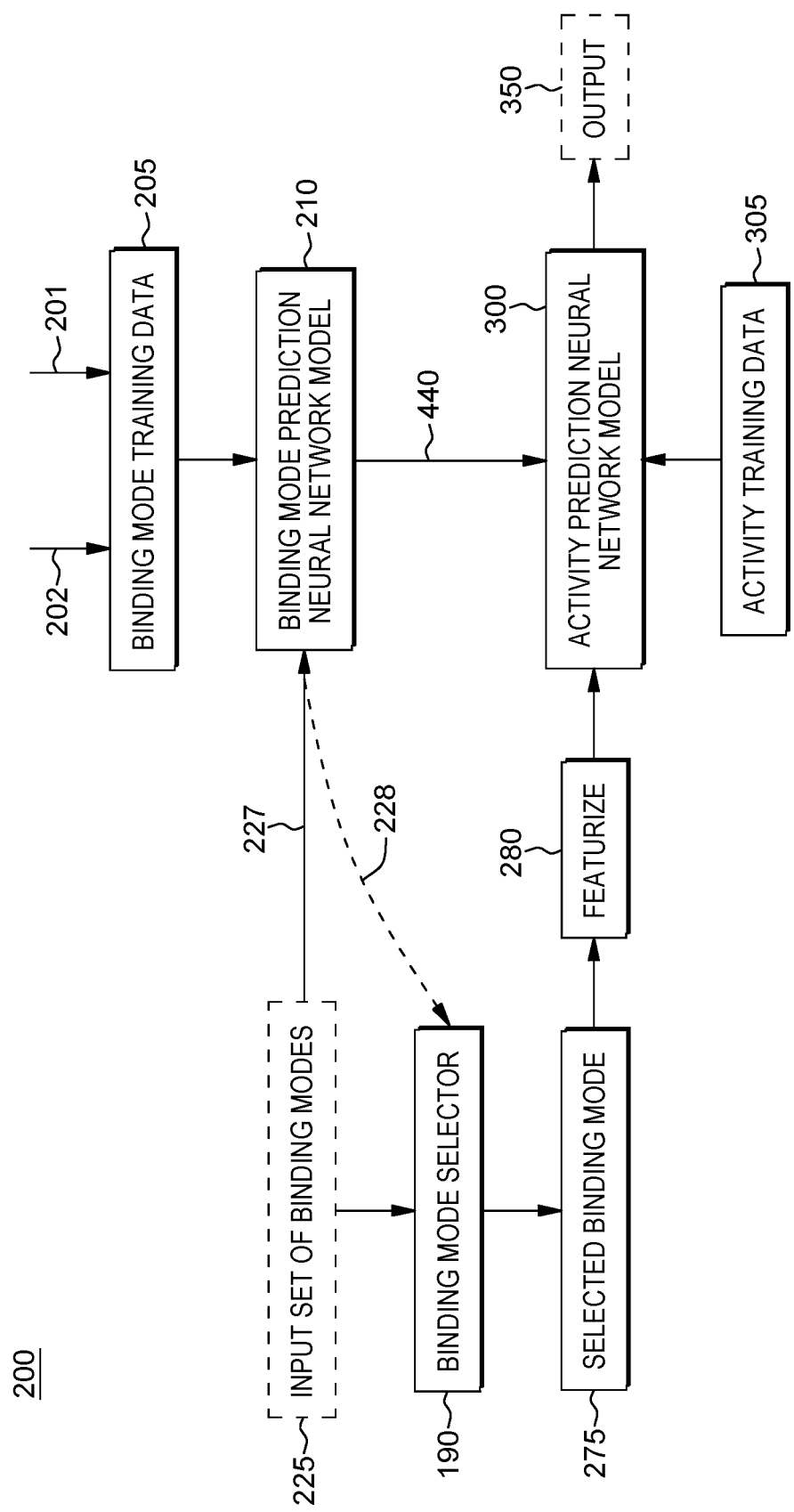
FIG. 3 is a schematic representation of a method run by supervisory program to automatically implement the tasks for more accurate small molecule activity prediction run by the system of FIG. 2.
Figure 8:
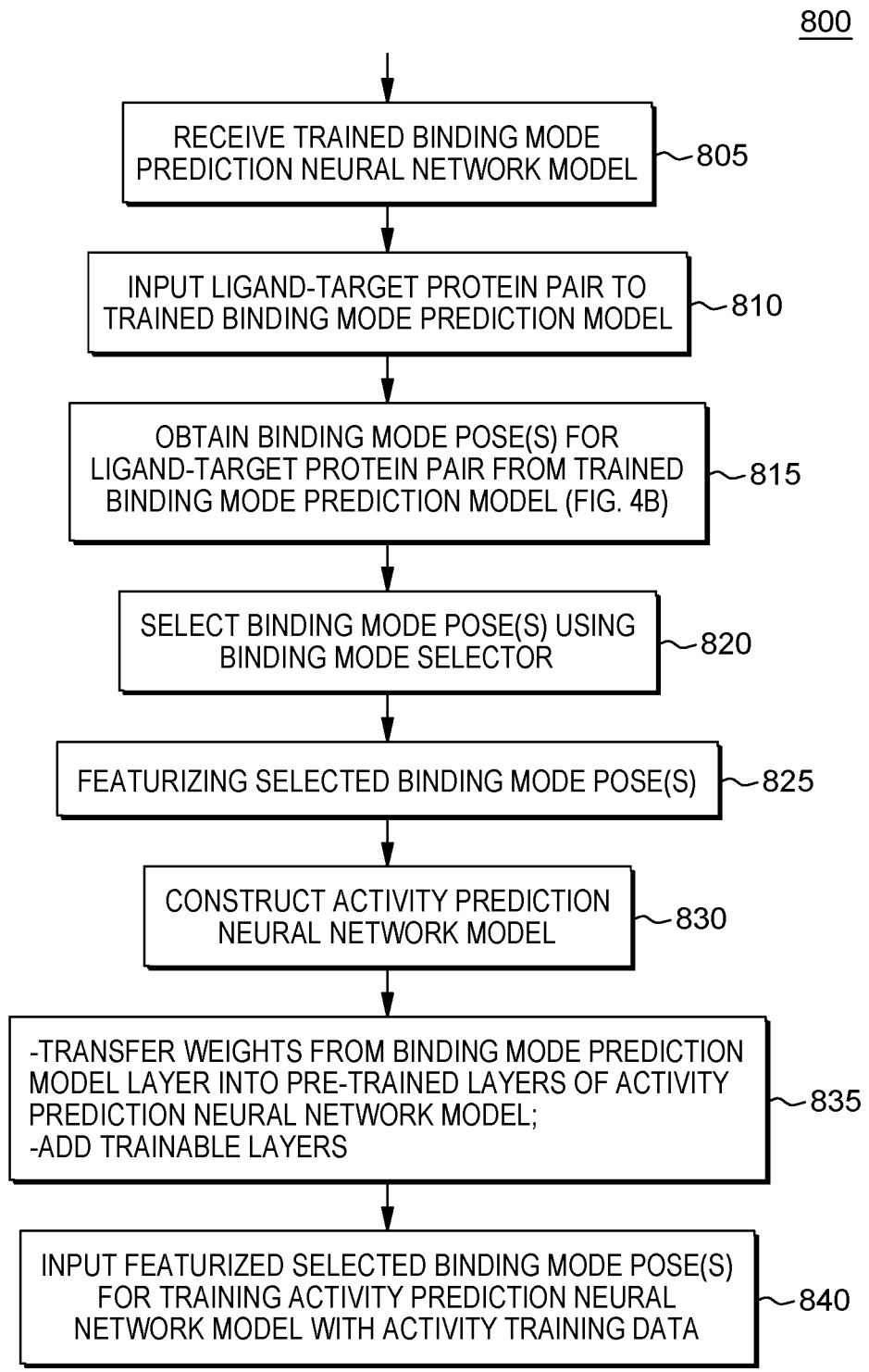
FIG. 8 is a flowchart depicting a method for target ligand-protein complex activity prediction by combining deep learning binding mode prediction with activity prediction models in an embodiment.

As further shown, memory 150 includes a supervisory program 110 having instructions for configuring the computing system 100 to invoke the improved activity prediction operations described herein with respect to FIGS. 3 and 8, i.e., provide application program interfaces for calling each of the program modules for small molecule activity prediction used to accelerate drug discovery.

FIG. 3 is a schematic representation of a method 200 run by supervisory program 110 to automatically implement the tasks for more accurate small molecule activity prediction run by system 100. In an embodiment, an input to the system includes: binding mode training data including a target protein(s) 201 and a ligand(s) 202 which are input to a docking program to generate a set of ligand-target protein complex binding modes 205 (e.g., three-dimensional coordinates representing ligand-protein poses or structures). Poses in the binding mode training set are labeled according to their distance from a reference structure. Alternately, for the ligand-target protein pair, the set of protein-ligand binding modes 205 (poses or structures) can be obtained from a database of crystal structures.

A binding mode prediction model 210 such as a graph CNN is then built that takes as training data input the binding mode (ligand-target protein) structures 205 and outputs a confidence measure that the input mode is in a correct conformation. The input binding mode is featurized as prescribed by the neural network, e.g., as a three-dimensional voxel-based image or a graph. This model is trained using supervised learning on a set of binding modes 205 labeled according to their closeness, i.e., distance, such as a root-mean-square deviation (RMSD) of atomic positions or like measure of an average distance, to an experimental reference set. In an embodiment, the data set used to train the binding mode prediction model at 210 may be 1) taken from a PDB database (www.rcsb.org and associated sites) and additional external or proprietary internal datasets; 2) structural data within a target family; or 3) an expanded training set constructed by assuming the binding pose for an active ligand from a crystal co-complex for a target is same in orthologs or homologs for which that ligand is also active. For training the binding mode prediction model, a combination of data sets 1) and 3) can be used or a combination of data sets 2) and 3) can be used for training.

As shown in FIG. 3, for ligand-protein activity prediction, the binding mode prediction model receives a set of binding modes 227 for a ligand-target protein pair related to a particular activity prediction problem (a second source of data). That is, for an activity prediction problem, a set of binding modes 227 needs to be input to the trained binding mode prediction model 210 that relate to activity prediction to get predictions of binding mode classifier as output 228 (received from the trained binding mode prediction model). When running an activity prediction problem, the binding mode prediction model 210 outputs binding mode confidence measures 228 (based on the input set of binding modes) which are input to the binding mode selector 190 for selection of reliable binding modes based on the particular activity prediction problem. The selected binding mode features are subsequently input to the activity prediction model 300.

Figure 4A:
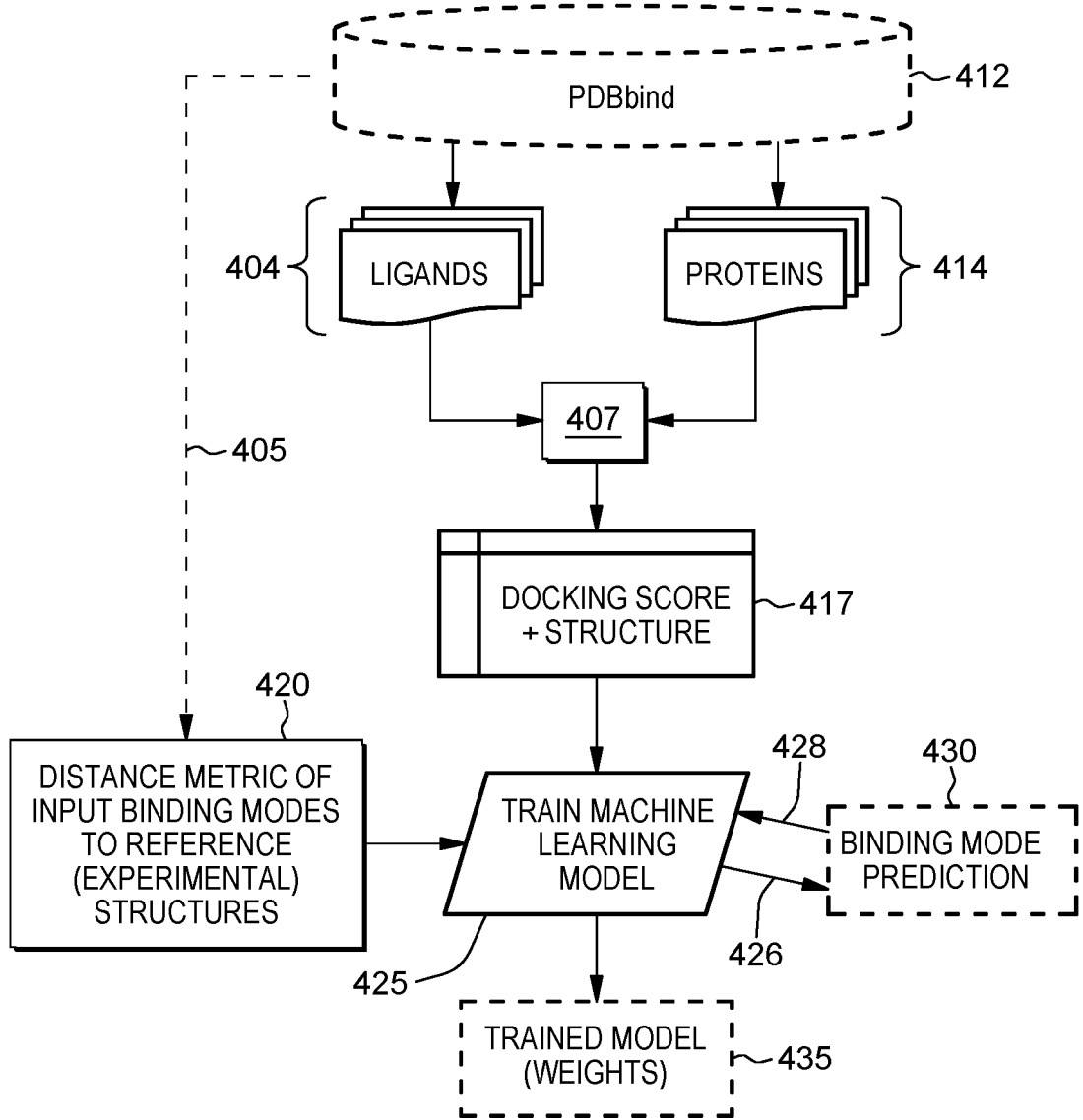
FIG. 4A shows an example implementation of a method run by the computer system of FIG. 2 for training a binding mode prediction model used to provide confidence measures from data representing protein-ligand structures.

FIG. 4A shows an example implementation of a method 400 run by the computer system of FIG. 2 for training a binding mode prediction model used to provide binding mode confidence measures from data representing known paired protein-ligand structures. Initially, a computer system, such as the system shown in FIG. 2, extracts training data sets that include protein-ligand pairs for which there are available distance measure labels 420 corresponding to the available experimental structures.

In an embodiment, the PDBbind or like database 412 provides known experimental ligand-protein pairs that have a corresponding distance measure 405 for each binding mode as determined by experiment which is used as a label 420 for supervised learning. A distance measure corresponding to each ligand-protein pair is input to the binding mode prediction model 425 being trained.

After the extracting each pair of the experimentally known small molecule(s) or ligand(s) 404 and target protein(s) 414, the method prepares structure files using an automated docking tool such as AutoDock Tools (e.g., available at autodock.scripps.edu). As known, the AutoDock Tools are software programs configured to prepare files that are needed to predict how small molecules, such as ligands, bind to a receptor of the known 3-D (e.g., target protein) structure.

Continuing in the method 400 of FIG. 4A, the method at 407 includes docking one or more of the ligands 404 towards the corresponding paired target protein structures 414 using AutoDock Vina tool with a fixed random seed and other default parameters. The AutoDock Vina program performs molecular docking that provides binding mode predictions, i.e., computing molecular docking scores 417 (or molecular binding affinity scores) and conformations between them. In one embodiment, for a ligand-target protein pair, a further output of the docking tool provides a binding mode structure, i.e., 3D graphic coordinates that describe the structure or orientation of a ligand with respect to its paired target protein (a binding mode or pose). In an embodiment, for its input and output, AutoDock Vina uses a PDBQT (Protein Data Bank, Partial Charge (Q), & Atom Type (T)) format) molecular structure file format used by AutoDock tools and AutoDock 4. All that is required is the structures of the ligands being docked and the specification of the search space including the target protein binding site. The docking scores and corresponding binding conformations are extracted and stored as ligand-target protein interaction feature set 417.

Based on the method steps of FIG. 4A after the generation of binding modes and docking scores from the docking program, in one embodiment, there is harvested a feature data matrix for use in training the binding mode prediction model. FIG. 5A is an example visualization of such a feature data matrix 500 (a 2-D matrix) that includes the ligands (e.g., drugs) 404 as rows, the paired target proteins 414 as columns, and the entries in the matrix are the featurized data as a graph 505 representing 3D coordinates of the binding mode of a paired protein-ligand pair obtained from a contact map, itself a 2-D matrix of known protein-ligand contacts. In this step, the binding mode graphs 505 for the interacting drugs/target proteins are the features forming the drug-target interaction feature set 417. In this embodiment, assuming a graph CNN binding mode prediction model, for this data set featurization, a method can first convert the 3D coordinates of the binding mode of the protein-ligand pair into a graph form (e.g., nodes that represent atoms, edges that represent either chemical bonds or contacts given by a contact map). These matrices can be sparse or dense, depending on the dataset that is employed.

For training the binding mode prediction model 425, the example feature data matrix 500 representing a formed drug-target interaction feature set 417 that includes the ligands (e.g., drugs) 404 as rows and paired target proteins 414 as columns, can alternatively, or in addition, include the individual docking scores obtained from the docking program as the features 505.

Returning to the method of FIG. 4A, in an embodiment, there is provided a step 420 for the generating of the labels for use in supervised training of the binding mode prediction model using the formed ligand-target molecule interaction feature set 417. At 420, for the binding mode prediction model, the training labels are generated by comparing the input binding modes with the known reference experimental binding mode using a distance measure. That is, the "binding modes" are defined as three-dimensional representations of the atomic coordinates of the target molecule interacting with the ligand molecule and can be characterized using the root-mean square deviation (RMSD) which measures the difference (in units of length) of the ligand's orientation and position relative to the target with respect to a reference structure. Accordingly, a "binding mode prediction" in the context herein is a prediction of the characterization of the sampled complexes (3D structures) formed between a ligand molecule and a target molecule (i.e., binding modes or poses). It should be noted that the binding mode prediction herein is not limited to the generation/sampling of binding modes but is also a prediction of their 'character' as related to ligand RMSD or other such measure.

FIG. 5B is an example visualization of a distance label training matrix 510 that includes ligand-target protein pairs 504 as rows and corresponding binding mode graphs 514 as columns corresponding to multiple binding modes. For each known ligand-target protein pair, the distance (e.g., using the RMSD distance measure) of the mode from a reference experimental binding mode forms a ligand-target protein pair training label 420. That is, the binding model prediction labels 420 are associated to the specific binding mode(s) of the known protein-ligand pair(s), i.e., the training labels depend on the orientation.

Returning to the method 400 of predicting binding mode confidence measures shown in FIG. 4A, in a subsequent process, at 425, the computer-implemented method includes developing and evaluating a graph CNN machine learned model 425 that can be used to predict a binding mode (pose confidence) 430 for any new ligand-protein pair based on the training sets of ligand-target protein binding mode interaction features and their corresponding known distance measure relationship labels 420. The binding mode prediction 430 represents an output layer (not shown) of the CNN model (which is the binding mode prediction) and is an argument to the loss function. The loss function measures how well the output layer reproduces the training labels and is minimized during training. The arrow 428 out of 425 to binding mode prediction 430 indicates that the output layer is the final result of the model and the arrow in 426 indicates it is used to compute a loss function and train the binding mode prediction model. Further, at 435, from the model binding mode prediction model, there is obtained a set of weights which, as shown in FIG. 3, become pre-trained weights 440 used as inputs to an activity prediction model.

Figure 6:
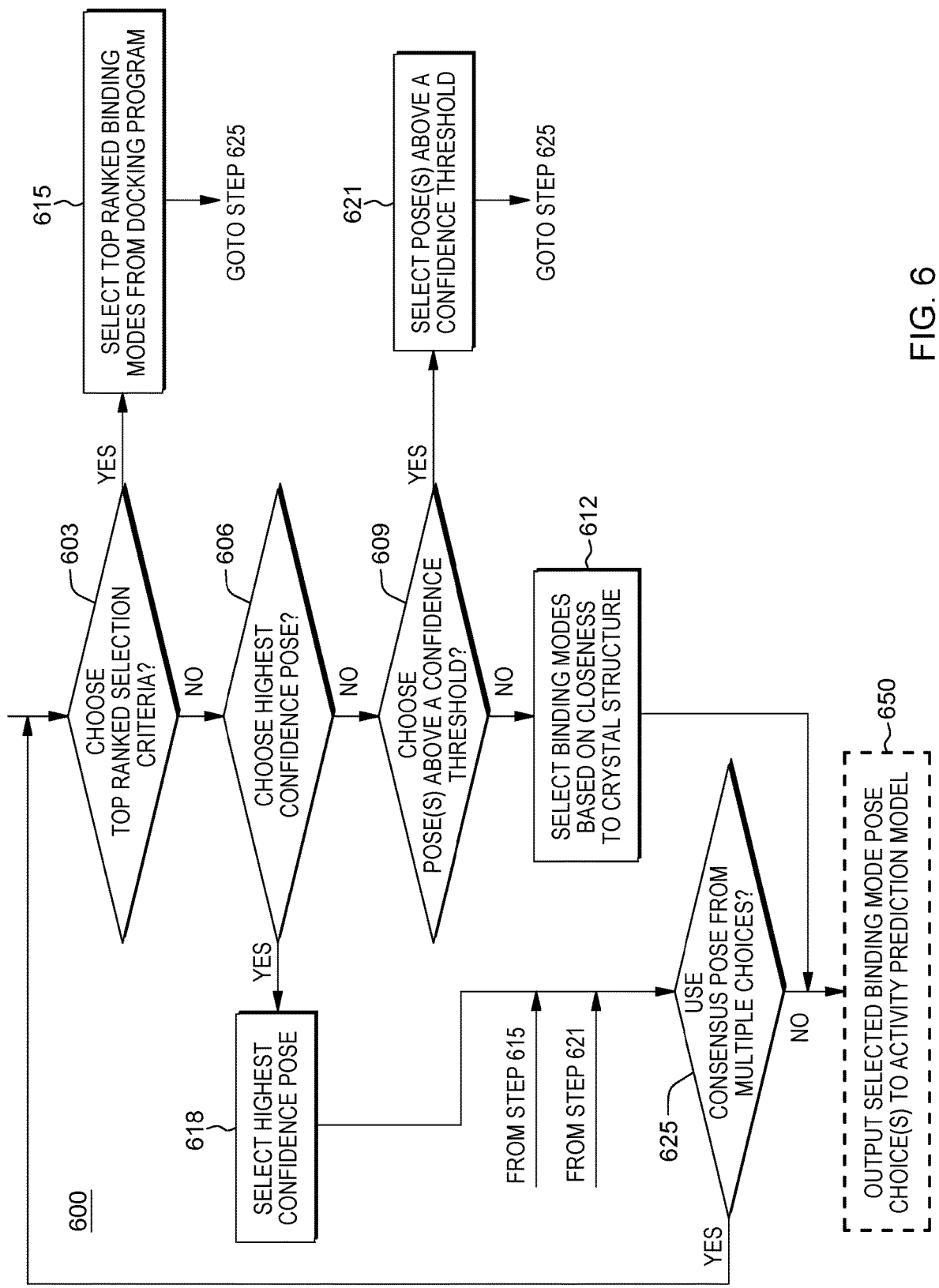
FIG. 6 depicts a method run by the binding mode selector module for choosing one or more reliable binding mode poses for input to the activity prediction model based on a binding mode selection criteria.

The trained model 435 is an output to the overall scheme that is used for transfer learning. This whole of the trained model is also used to produce a binding mode prediction (FIG. 4B) for the binding mode selector (FIG. 6).

Returning to FIG. 3, the method 200 further includes generating an activity prediction model 300 based on input activity training data 305 and labels. In particular, supervisory program 110 runs method steps to automatically implement the tasks for building a deep neural network activity prediction model to predict if a ligand is active against a particular protein including when there is no crystal reference for this pair. In an embodiment, the system constructs an activity prediction model 300 as a deep neural network composed of: 1) one or more pre-trained layers whose weights 440 are obtained from the trained binding mode prediction model with compatible architecture (i.e., Transfer Learning) and are constrained or frozen for the task of activity prediction; and 2) additional task-specific, trainable layers for activity prediction. In an embodiment, the activity prediction model is trained on data including, but not limited to: docked structures corresponding to ligand-protein pairs and their corresponding activity data used as training labels. The trained activity prediction model is configured to output an activity prediction 350.

The activity prediction model 300 is trained based on activity training datasets 305 that include selected ligand-target molecule (protein) pair(s), e.g., from high-throughput (HTS) screening data. The activity prediction model can be trained based on target protein data from choices including: 1) a single protein target; 2) targets within a protein family; or 3) a number of protein targets sampled across protein families. For example, activity prediction model training can be focused on single target protein data, or focused on specific target family data.

In an embodiment, the activity training labels are associated to a ligand-target protein pair. The activity data for use as labels for training the activity prediction model 300 can be obtained from extensive experimental sources, e.g. high-throughput screening assays, and can include, but not limited to: the IC50 measure of the effectiveness of a substance in inhibiting a specific biological or biochemical function; EC50 measure is the concentration of a drug that gives half-maximal response; the disassociation constant (Kd) which defines the likelihood that an interaction between two molecules will break; the binding affinity inhibitory constant (Ki) measure, etc. In embodiments, other measures of activity that serve as training labels for the activity prediction model can be used.

As further shown in FIG. 3, in an embodiment, binding mode poses 225, similarly used as inputs 227 for training the binding mode prediction model and related to the particular activity prediction, are selected for input into the activity prediction model. The selection of binding mode poses 225 is performed by a method run at the binding mode selector module 190.

Figure 4B:
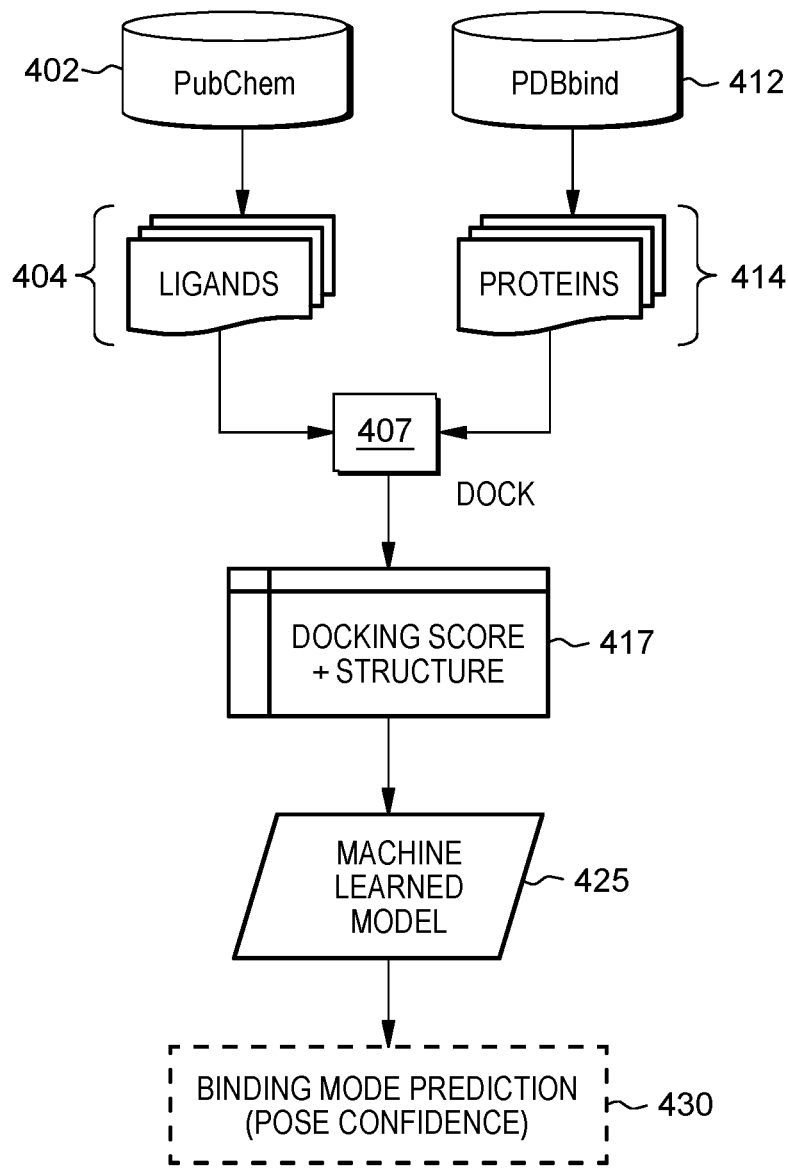
FIG. 4B shows an example implementation of running the trained binding mode prediction model to provide binding mode confidences of a ligand-target molecule structure for use in activity prediction model training.

FIG. 4B shows an example implementation of a method 401 running the trained binding mode prediction model 430 to provide binding mode confidences of a ligand-target molecule structure for use in activity prediction model training.

As shown in FIG. 4B, data representing 3-D ligand structures 404 and corresponding target molecules (e.g, proteins) 414 from the PDBbind database 412 are input to a molecular docking program 407 for generating a ligand-target molecule interaction feature, i.e., a molecular binding mode graph or docking score. In one embodiment, the method includes extracting a 3-D structure(s) of ligand molecules 404 from a database such as the commercially available PubChem® database resource 402 (e.g., available at pubchem.ncbi.nlm.nih.gov) or PDBbind database 412. In one embodiment, to obtain a set of ligands 404, the computer system harvests the SMILES (Simplified Molecular-Input Line-Entry System) notation used for encoding molecular structures of all the small molecules in PubChem® database resource 402. The small molecules or ligands can also include molecule structures derived from other sources, e.g., proprietary structures.

In a further embodiment, for the ligand molecules in the data set 404, the computer system accesses tools for generating associated 3D molecular structures based on an input chemical formula or drawing representing a 2-D molecule. The 3D molecular structures can represent ligands and can have rotatable bonds. The 3-D drug molecules can be in various file formats, e.g., molecule file formats, graphics formats etc.

As further shown in FIG. 4B, the computer system further obtains data representing the plurality of protein structures 414. For exemplary purposes, human proteins are used but alternate embodiments may be adapted for other animal protein types. For the protein set 414, the system can harvest a general collection of the PDBbind database resource 412 (e.g., available at www.pdbbind.org.cn) or like protein data bank (PDB), which is a curated source of crystal structures. Human proteins 414 can be selected and one or more unique structures for each protein can be selected. Via a computer system interface, a user may select a particular protein, e.g., by entering via an interface to the PDBbind database resource 412 according to a resolution, a PD, a unique selection, and a PDBbind criteria. The selected proteins 414 for modeling can include structures derived from other sources, e.g., proprietary structures.

In one embodiment, extracted from the PDBbind database 412, are data representing unique human protein targets and the target proteins are selected from the PDBbind database 412 according to a selected criteria, including but not limited to: (1) a quality, i.e., an extracted protein structure has a high resolution; (2) is targetable, i.e., the structures can have experimental ligand binding data available; and (3) have well-defined binding pockets.

The selected ligand-target molecule data pair(s) from both PubChem® and PDBbind are inputs to the overall activity prediction scheme. That is, they are run through the already built (trained) binding mode prediction (BMP) model 425 which provides the corresponding binding mode (pose) confidence for the particular input ligand-target molecule pair. The output 430 of the binding mode prediction model 425 yields a prediction used by the binding mode selector 190.

In an embodiment, the binding mode selector module 190 chooses reliable binding mode poses from binding prediction mode model BMP outputs 228 for input ligand-target molecule pairs. The binding mode selector module can use the binding mode prediction model to choose poses, and/or employ direct comparisons with experiment and/or consensus models.

FIG. 6 depicts a method 600 run by the binding mode selector module 190 for choosing one or more reliable binding mode poses for input to the activity prediction model based on a binding mode selection criteria selected by a user. At 603, the method 600 first determines whether a top ranked binding mode selection criteria has been chosen based on the docking scoring function of the docking program. If this top ranked selection criteria has been chosen at 603, then at 615, the method selects the top ranked binding modes from the docking program, and the method proceeds to step 625. Otherwise, at 603, if the top ranked selection criteria has not been chosen, then the process proceeds to 606 where a determination is made as to whether a highest confidence binding pose criterion as predicted from output of the binding mode prediction model has been chosen. If a highest confidence binding pose criterion has been chosen, then at 618, the method selects a highest confidence binding pose and the method proceeds to step 625. Otherwise, at 606, if the highest confidence binding pose criterion has not been chosen, then the process proceeds to 609 where a determination is made as to whether a binding mode pose(s) above a pre-specified confidence threshold as determined by the binding mode prediction model output has been chosen. If a binding mode pose(s) above the pre-specified confidence threshold has(have) been chosen, then at 621, the method selects a pose(s) above the specified confidence threshold and the method proceeds to step 625. Otherwise, at 609, if the binding mode pose(s) above a pre-specified confidence threshold has not been chosen, then the method proceeds to step 612, FIG. 6 where the method selects binding modes based on closeness to the crystal structure. That is, a protein-ligand binding mode(s) is selected that is(are), or is(are) close to, experimentally determined crystal structures of same or closely related target-ligand pairs. If, at 612, a protein-ligand binding mode(s) is selected that is(are), or is(are) close to, experimentally determined crystal structure, then the process proceeds to step 650 where the selected binding mode prediction choice is output for featurization and input to activity prediction model and the process ends.

In an embodiment, a consensus binding pose can be selected as defined by comparison of poses generated by, for example, single docking program using different crystal structures of same target protein or similar ligands or similar target proteins; or a single target-ligand pair but different docking programs; and the preceding combined with other options at steps 615, 618 and 621. As binding mode selection can be based on a consensus of the poses, then at step 625, a determination is made as to whether a consensus pose from at least two or more of the selection criteria are to be used for output to the activity prediction model. If a consensus for selecting poses is chosen, then the process returns to step 603 to repeat selecting any additional binding mode choices at one or more steps of 615, 618 or 621. After one or several more iterations of binding pose selection, upon returning to step 625, once each of the consensus choices of the various binding pose(s) have been selected, the binding pose choices are returned for output featurization and input to the activity prediction model at 650.

Returning back to FIG. 3, the selected binding mode pose 275 using the selector 190 is then featurized at 280 for input to the activity prediction model 300 as additional training data for more accurate prediction of biological activity of an input ligand-target protein molecule pair. The selected input binding mode is featurized as prescribed by the neural network: e.g., a three-dimensional voxel-based image or a graph. In embodiments, both the binding mode and activity prediction model have a similar featurization procedure depending on the form of the neural networks (e.g., if both are graph CNNs) where 3-D coordinates are converted into a set of graphs, with atoms given a set of features.

Figure 7B:
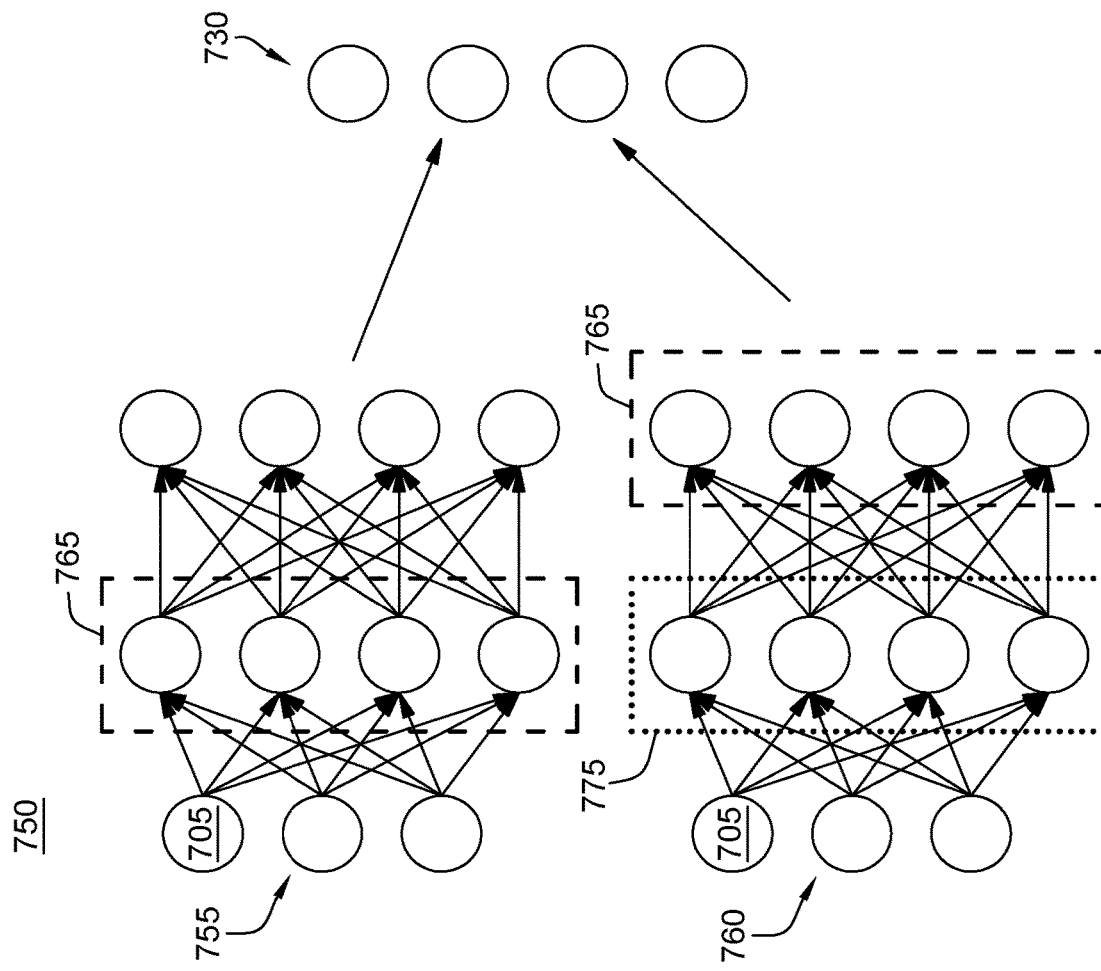
FIGS. 7A and 7B depict example deep neural networks (DNNs) used as an activity prediction model according to one or more embodiments.
Figure 7A:
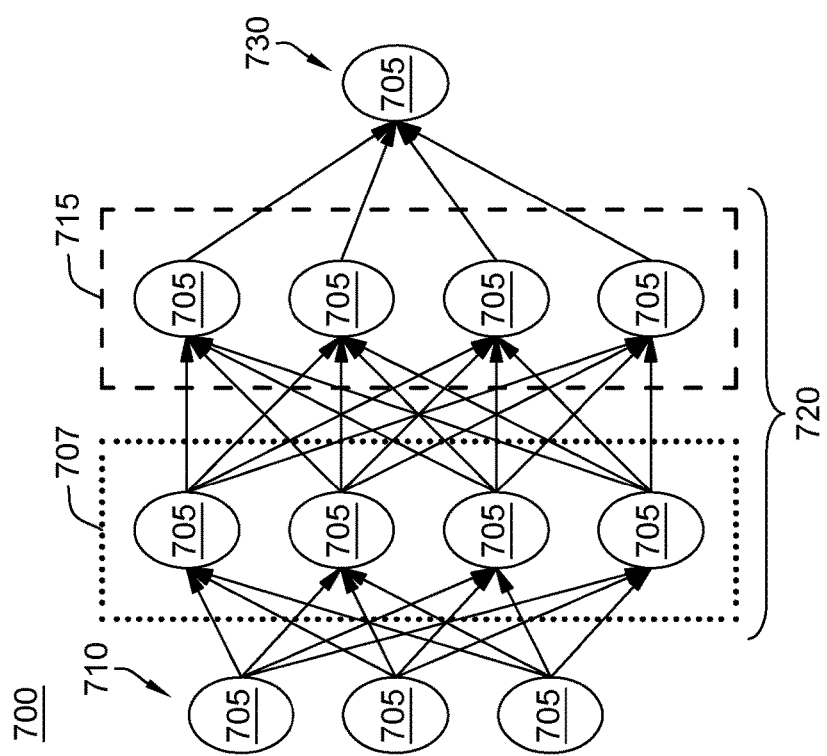

The activity prediction model 300 is then built and trained as a deep neural network, e.g., a graph CNN. FIGS. 7A and 7B depict example deep neural network schematics for use as an activity prediction model according to one or more embodiments.

The example activity prediction DNN model 700 of FIG. 7A includes multiple (two or more) layers of neurons 705 between the input layer 710 and output layer 720, where each layer of nodes trains on a distinct set of features based on the previous layer's output. The input layer has its own weights that multiply the incoming data. The input layer then passes the data through the activation function before passing it on. The data is then multiplied by the first hidden layer's weights. The further (to the right in FIG. 7A) the layer in the DNN 700, the more complex the features the nodes can recognize, because the layers aggregate and recombine features from the previous layer(s). This feature hierarchy of increasing complexity and abstraction makes the DNN 700 capable of handling very large, high-dimensional data sets with billions of parameters that pass through nonlinear functions.

When training, the DNN 700 can learn to recognize correlations between certain relevant features and optimal results—by drawing connections between feature signals and what those features represent with labeled data. The DNN 700 ends in an output layer 730: a logistic, or softmax, classifier that assigns a likelihood to a particular outcome or label.

As the DNN 700 is shown in FIG. 7A to include only two hidden layers 720, in other examples, the DNN 700 can include any number of hidden layers 720 greater than two. In an embodiment, the input and/or hidden layers can comprise a pre-trained layer 707, i.e., a "frozen" layer with weights determined by training on a first task (i.e., binding mode prediction) and a trainable layer 715 that are trained using the data/labels specific to the activity prediction task. That is, selected weights/neural network layers from the binding mode prediction model are 'transferred' into the activity prediction model as frozen layers/weights. As shown in DNN 700 of FIG. 7, the "deeper" (closer to the input) layers in the network are frozen and later layers are trainable.

As shown in FIG. 7B, an activity prediction DNN model 750 is split into two portions 755, 760, from which only one portion of input at bottom row 760 has a frozen layer 775 in the "deepest" parts of the network for receiving input relating to the binding mode prediction. The deep layers 765 that interact with the top input portion 755 are fully trainable.

In both DNN model implementations 700, 750, the pre-trained and task-specific layers of the generated activity prediction model 700 can be arranged in different ways, e.g., sequentially or in parallel.

FIG. 8 is a flowchart depicting a method 800 for target ligand-protein complex activity prediction by combining deep learning binding mode prediction with activity prediction models. Step 805 depicts the receiving a trained binding prediction neural network model into the computer system. In an embodiment, the trained binding mode prediction model is a graph convolutional neural network acting on a ligand-protein contact map. Then, at 810, the method inputs a ligand-target protein pair related to activity prediction into the trained binding mode prediction model and performs method steps of FIG. 4B. Depending upon whether the binding mode prediction model is trained with suitable PDB structures, e.g., from proteins within a target family, or is trained with expanded training data set using protein orthologs or homologs where the ligand is active, there is obtained at 815, FIG. 8, one or more binding mode pose(s) for the ligand-target protein pair related to activity prediction output from the trained binding mode prediction model. Then, at 820, FIG. 8, the binding mode selector selects a binding mode pose for use in activity prediction. At 825, FIG. 8, the selected binding mode pose is featurized, i.e., represented as a voxel-image or graph for a graph-based CNN. At 830, the method constructs an activity prediction model that, in an example implementation, is also a graph convolutional neural network acting on a ligand-protein contact map. At step 835, FIG. 8, in the construction of the activity prediction DNN model, the system performs steps of transferring weights from the trained binding mode prediction model layers into a pre-trained layer(s) of the activity prediction neural network model. Additional task-specific, trainable layers for activity prediction are further added to the activity prediction model. The pre-trained layers and task-specific layers can be arranged in different ways, e.g., sequentially or in parallel. Then, at 840, the method inputs featurized selected binding mode pose(s) into the activity prediction neural network model and the activity prediction model is trained based on activity training data and selected binding mode pose(s) of ligands-target proteins.

In an embodiment, the trained activity prediction neural network model trained using activity training data and selected binding poses of ligands-target proteins can be formulated to more accurately perform a classification (e.g., active, inactive predictions), a regression (e.g., binding affinity, IC50, etc.), or can encompass both on- and off-target activities, and thus can predict a characteristic such as toxicity or metabolism.

Then, to solve an activity prediction problem, given an input ligand-target protein pair, e.g., where the ligand is a ligand of a new drug compound, a docking program is first used to obtain a set of binding modes or poses. Then the binding mode selector is invoked to select a reliable set of binding modes (e.g., related to the input ligand-target protein pair). This set of selected binding modes are featurized and run through the trained activity prediction model with layers based on weights from the binding mode predictor. The model then outputs an activity prediction, e.g., or obtain a classification or a regression with improved accuracy. The improved activity prediction model obtains an output answering a question if the ligand is an active molecule or not, or obtain a ranking of activities for use in virtual screening.

The use of transfer learning with activity prediction models (e.g., for single target proteins) trained on single target protein data for a series of target proteins improves average performance over multiple single target models built from HTS assay data using protein-ligand features alone. For example, single target models built from an HTS assay data, certain target proteins, the use of transfer learning improves an average AUC performance.

The system and method for target ligand-protein complex activity prediction by combining deep learning binding mode prediction with activity prediction models can benefit anyone engaged in drug discovery (pharmaceutical companies, biotechnology companies, etc.) however could expand to other industries (e.g., food science, fragrances, agriculture) interested in the interaction of ligands with target molecules, as well.

Figure 9:
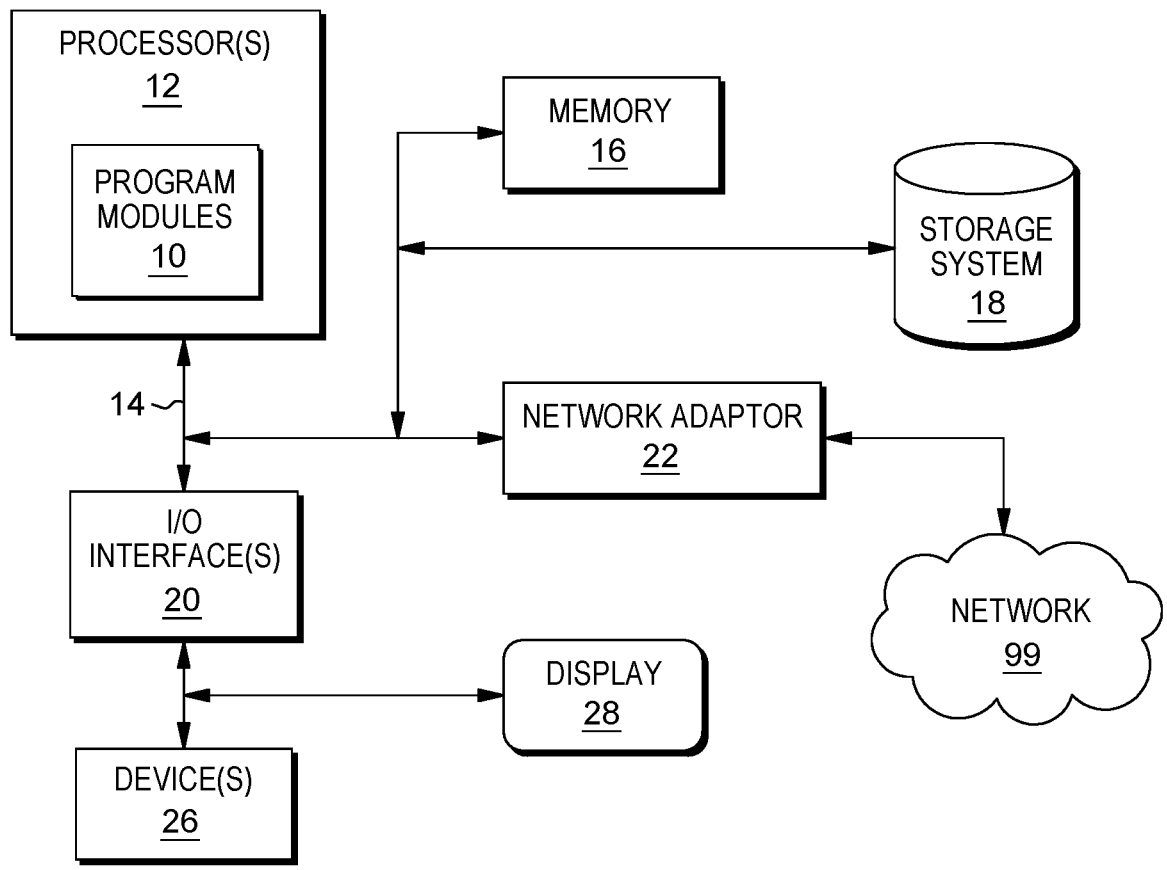
FIG. 9 schematically shows an exemplary computer system/computing device which is applicable to implement the embodiments of the present invention.

FIG. 9 illustrates an example computing system in accordance with the present invention. It is to be understood that the computer system depicted is only one example of a suitable processing system and is not intended to suggest any limitation as to the scope of use or functionality of embodiments of the present invention. For example, the system shown may be operational with numerous other general-purpose or special-purpose computing system environments or configurations. Examples of well-known computing systems, environments, and/or configurations that may be suitable for use with the system shown in FIG. 9 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

In some embodiments, the computer system may be described in the general context of computer system executable instructions, embodied as program modules stored in memory 16, being executed by the computer system. Generally, program modules may include routines, programs, objects, components, logic, data structures, and so on that perform particular tasks and/or implement particular input data and/or data types in accordance with the present invention (see e.g., FIG. 2).

The components of the computer system may include, but are not limited to, one or more processors or processing units 12, a memory 16, and a bus 14 that operably couples various system components, including memory 16 to processor 12. In some embodiments, the processor 12 may execute one or more modules 10 that are loaded from memory 16, where the program module(s) embody software (program instructions) that cause the processor to perform one or more method embodiments of the present invention. In some embodiments, module 10 may be programmed into the integrated circuits of the processor 12, loaded from memory 16, storage device 18, network 24 and/or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system may include a variety of computer system readable media. Such media may be any available media that is accessible by computer system, and it may include both volatile and non-volatile media, removable and non-removable media.

Memory 16 (sometimes referred to as system memory) can include computer readable media in the form of volatile memory, such as random access memory (RAM), cache memory an/or other forms. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

The computer system may also communicate with one or more external devices 26 such as a keyboard, a pointing device, a display 28, etc.; one or more devices that enable a user to interact with the computer system; and/or any devices (e.g., network card, modem, etc.) that enable the computer system to communicate with one or more other computing devices. Such communication can occur via Input/Output (I/O) interfaces 20.

Still yet, the computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with the computer system. Examples include, but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The corresponding structures, materials, acts, and equivalents of all elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer-implemented method of predicting an activity of a ligand against a target molecule, the method comprising:
    receiving, at a hardware processor, a representation of a ligand molecule and a target molecule forming a ligand-target molecule pair structure for which an activity is to be determined;
    obtaining, at the hardware processor, one or more binding modes corresponding to the received ligand-target molecule pair structure;
    determining, using a first neural network running at the hardware processor, a confidence metric characterizing a correctness of each of the obtained one or more binding modes, said first neural network comprising a deep neural network model trained to predict a characterizing confidence metric using labels representing a closeness of binding modes corresponding to training sets of ligand-target molecule pair structures to a reference set of binding modes;
    selecting, using the hardware processor, one or more binding modes based on their corresponding characterizing metrics;
    inputting, to a second neural network running at the hardware processor, as input features, the selected one or more binding modes, said second neural network comprising a deep neural network of a compatible structure as said first neural network, said second neural network trained to predict an activity based on training sets of ligand-target molecule pair structures and corresponding labels representing their known activities;
    determining, using the second neural network, a prediction of an activity for said ligand-target molecule pair structure; and
    outputting, by the hardware processor, the activity prediction for said ligand-target molecule pair structure, wherein said output activity prediction is formulated as a classification or a regression with improved accuracy.

2. The method as claimed in claim 1, wherein the second neural network model comprises:
    one or more pre-trained processing layers having weights obtained from the trained first neural network; and
    additional task-specific, trainable layers for activity prediction.

3. The method as claimed in claim 1, wherein the one or more binding modes are obtained using one of: a docking program or a database of crystal structures.

4. The method as claimed in claim 3, wherein said selecting one or more binding modes based on their corresponding characterizing metric comprises one or more of:
    selecting a top-ranked pose predicted by a docking scoring function;
    selecting a binding mode having a highest confidence metric as predicted from an output of the first neural network;
    selecting a pre-determined number of top binding modes above a confidence metric threshold as determined from the output of the first neural network;
    selecting one or more ligand-target molecule binding modes that are, or are close to, experimentally determined structures of same or closely related ligand-target molecule pairs; or
    selecting a binding mode based on a consensus achieved by comparison of binding modes generated by other means.

5. The method as claimed in claim 1, further comprising training said first neural network and second neural network using datasets comprising data corresponding to one or more of: a single protein target, targets within a protein family, or a number of targets sampled across multiple protein families, additional types of molecular targets and a set of associated ligands.

6. The method as claimed in claim 1, wherein said first neural network deep neural network model is trained using training data constructed as a training set of binding poses in which the binding pose for an active ligand from a crystal co-complex for a target is the same in orthologs or homologs for which that active ligand is also active.

7. The method as claimed in claim 1, further comprising:
featurizing a selected binding mode pose by representing the binding mode pose as a voxel image or a graph; and
inputting featurized selected binding mode poses as said input features for training said second neural network model.

8. A non-transitory computer readable medium comprising instructions that, when executed by at least one hardware processor, configure the at least one hardware processor to:
receive a representation of a ligand molecule and a target molecule forming a ligand-target molecule pair structure for which an activity is to be determined;
obtain one or more binding modes corresponding to the received ligand-target molecule pair structure;
determine, using a first neural network, a confidence metric characterizing a correctness of each of the obtained one or more binding modes, said first neural network comprising a deep neural network model trained to predict a characterizing confidence metric using labels representing a closeness of binding modes corresponding to training sets of ligand-target molecule pair structures to a reference set of binding modes;
select one or more binding modes based on their corresponding characterizing metrics;
input, to a second neural network, as input features, the selected one or more binding modes, said second neural network comprising a deep neural network of a compatible structure as said first neural network, said second neural network trained to predict an activity based on training sets of ligand-target molecule pair structures and corresponding labels representing their known activities;
determine, using the second neural network, a prediction of an activity for said ligand-target molecule pair structure; and
output the activity prediction for said ligand-target molecule pair structure, wherein said output activity prediction is formulated as a classification or a regression with improved accuracy.

9. The non-transitory computer readable medium as claimed in claim 8, wherein the second neural network model comprises:
one or more pre-trained processing layers having weights obtained from the trained first neural network; and
additional task-specific, trainable layers for activity prediction.

10. The non-transitory computer readable medium as claimed in claim 8, wherein the one or more binding modes are obtained using one of: a docking program or a database of crystal structures.

11. The non-transitory computer readable medium as claimed in claim 10, wherein to select one or more binding modes based on their corresponding characterizing metric, the at least one hardware processor is further configured to:
select a top-ranked pose predicted by a docking scoring function;
select a binding mode having a highest confidence metric as predicted from an output of the first neural network;
select a pre-determined number of top binding modes above a confidence metric threshold as determined from the output of the first neural network;
select one or more ligand-target molecule binding modes that are, or are close to, experimentally determined structures of same or closely related ligand-target molecule pairs; or
select a binding mode based on a consensus achieved by comparison of binding modes generated by other means.

12. The non-transitory computer readable medium as claimed in claim 8, wherein the at least one hardware processor is further configured to:
train said first neural network and second neural network using datasets comprising data corresponding to one or more of: a single protein target, targets within a protein family, or a number of targets sampled across multiple protein families, additional types of molecular targets and a set of associated ligands.

13. The non-transitory computer readable medium as claimed in claim 8, wherein the at least one hardware processor is further configured to:
train said first neural network deep neural network model using training data constructed as a training set of binding poses in which the binding pose for an active ligand from a crystal co-complex for a target is the same in orthologs or homologs for which that active ligand is also active.

14. The non-transitory computer readable medium as claimed in claim 8, wherein the at least one hardware processor is further configured to:
featurize a selected binding mode pose by representing the binding mode pose as a voxel image or a graph; and
input featurized selected binding mode poses as said input features for training said second neural network model.

15. A computer system for predicting an activity of a ligand against a target molecule, the system comprising:
a memory storage device; and
a hardware processor coupled to said memory storage device and configured to perform a method to:
receive a representation of a ligand molecule and a target molecule forming a ligand-target molecule pair structure for which an activity is to be determined;
obtain one or more binding modes corresponding to the received ligand-target molecule pair structure;
determine, using a first neural network, a confidence metric characterizing a correctness of each of the obtained one or more binding modes, said first neural network comprising a deep neural network model trained to predict a characterizing confidence metric using labels representing a closeness of binding modes corresponding to training sets of ligand-target molecule pair structures to a reference set of binding modes;
select one or more binding modes based on their corresponding characterizing metrics;
input, to a second neural network, as input features, the selected one or more binding modes, said second neural network comprising a deep neural network of a compatible structure as said first neural network, said second neural network trained to predict an activity based on training sets of ligand-target molecule pair structures and corresponding labels representing their known activities;

determine, using the second neural network, a prediction of an activity for said ligand-target molecule pair structure; and output the activity prediction for said ligand-target molecule pair structure, wherein said output activity prediction is formulated as a classification or a regression with improved accuracy.

16. The computer system as claimed in claim 15, wherein the second neural network model comprises:

one or more pre-trained processing layers having weights obtained from the trained first neural network; and additional task-specific, trainable layers for activity prediction.

17. The computer system as claimed in claim 15, wherein the one or more binding modes are obtained using one of: a docking program or a database of crystal structures.

18. The computer system as claimed in claim 17, wherein to select one or more binding modes based on their corresponding characterizing metric, the hardware processor is further configured to one or more of:

select a top-ranked pose predicted by a docking scoring function;

select a binding mode having a highest confidence metric as predicted from an output of the first neural network;

select a pre-determined number of top binding modes above a confidence metric threshold as determined from the output of the first neural network;

select one or more ligand-target molecule binding modes that are, or are close to, experimentally determined structures of same or closely related ligand-target molecule pairs; or select a binding mode based on a consensus achieved by comparison of binding modes generated by other means.

19. The computer system as claimed in claim 15, wherein the hardware processor is further configured to:

train said first neural network deep neural network model using training data constructed as a training set of binding poses in which the binding pose for an active ligand from a crystal co-complex for a target is the same in orthologs or homologs for which that active ligand is also active.

20. The computer system as claimed in claim 15, wherein the hardware processor is further configured to:

featurize a selected binding mode pose by representing the binding mode pose as a voxel image or a graph; and input featurized selected binding mode poses as said input features for training said second neural network model.

* * * * *